United States Patent [19]

Alterbaum

[11] Patent Number: 4,714,457
[45] Date of Patent: Dec. 22, 1987

[54] METHOD AND APPARATUS FOR USE IN PREPARATION OF FIBRINOGEN FROM A PATIENT'S BLOOD

[76] Inventor: Robert Alterbaum, 101 West 15th St., New York, N.Y. 10011

[21] Appl. No.: 906,894

[22] Filed: Sep. 15, 1986

[51] Int. Cl.⁴ .................. B04B 5/02; B01D 43/00
[52] U.S. Cl. ............................. 494/37; 494/20; 494/21; 494/45
[58] Field of Search ................ 494/16, 17, 18, 20, 494/21, 27, 3.7, 45, 74, 79; 604/4, 5, 6; 128/334 R, DIG. 22

[56] References Cited

U.S. PATENT DOCUMENTS 4,253,458  5/1981  Bacehowski et al. ............ 604/6
4,303,193  12/1981 Latham, Jr. ..................... 494/27
4,413,773  11/1983 Rohde et al. .................... 494/20
4,617,009  10/1986 Öhlin et al. ...................... 494/21

Primary Examiner—Timothy F. Simone
Assistant Examiner—Corinne Reinckens
Attorney, Agent, or Firm—Steinberg & Raskin

[57] ABSTRACT

In the preparation of concentrated fibrinogen extracted from the blood for making fibrin glue for use, e.g., as tissue adhesive or intra-arterial embolizing agent, the blood and subsequently obtained plasma are separated by centrifuging. In order to efficiently and rapidly prepare a small quantity of fibrinogen from a patient's own blood to be administered to the same patient during imminent surgery, an arrangement is disclosed wherein the blood or plasma to be centrifuged is transferred to a flat bag or packet which is then fitted into an insert fixture assembly which reliably secures the packet in the centrifuge cup in a suitable orientation.

8 Claims, 5 Drawing Figures

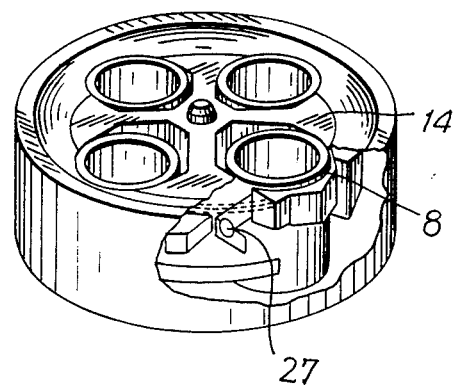
FIG. 2
FIG. 3
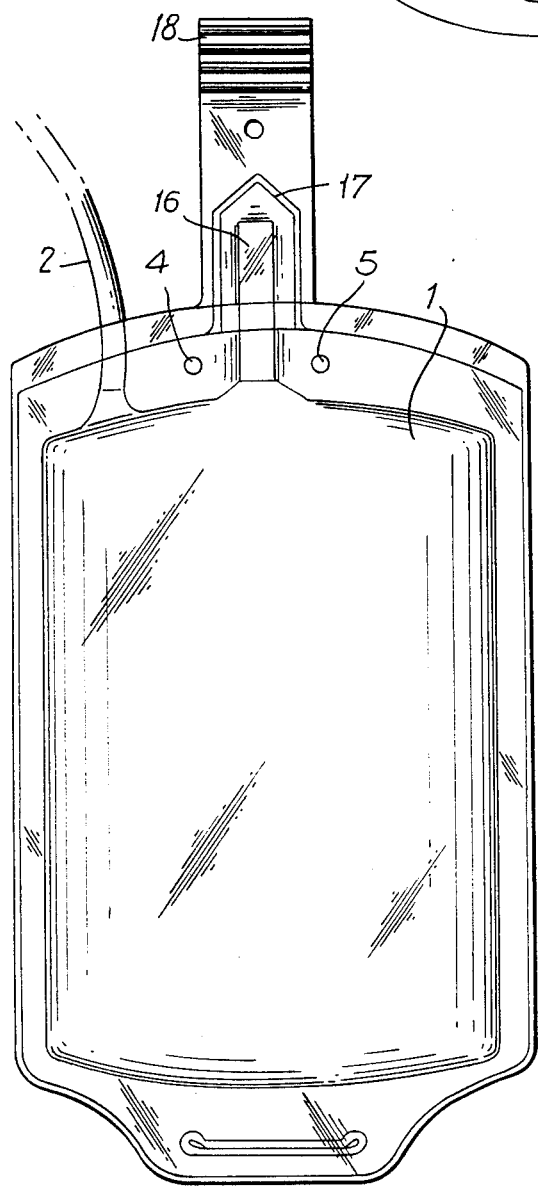

U.S. Patent  Dec. 22, 1987  Sheet 3 of 3  4,714,457
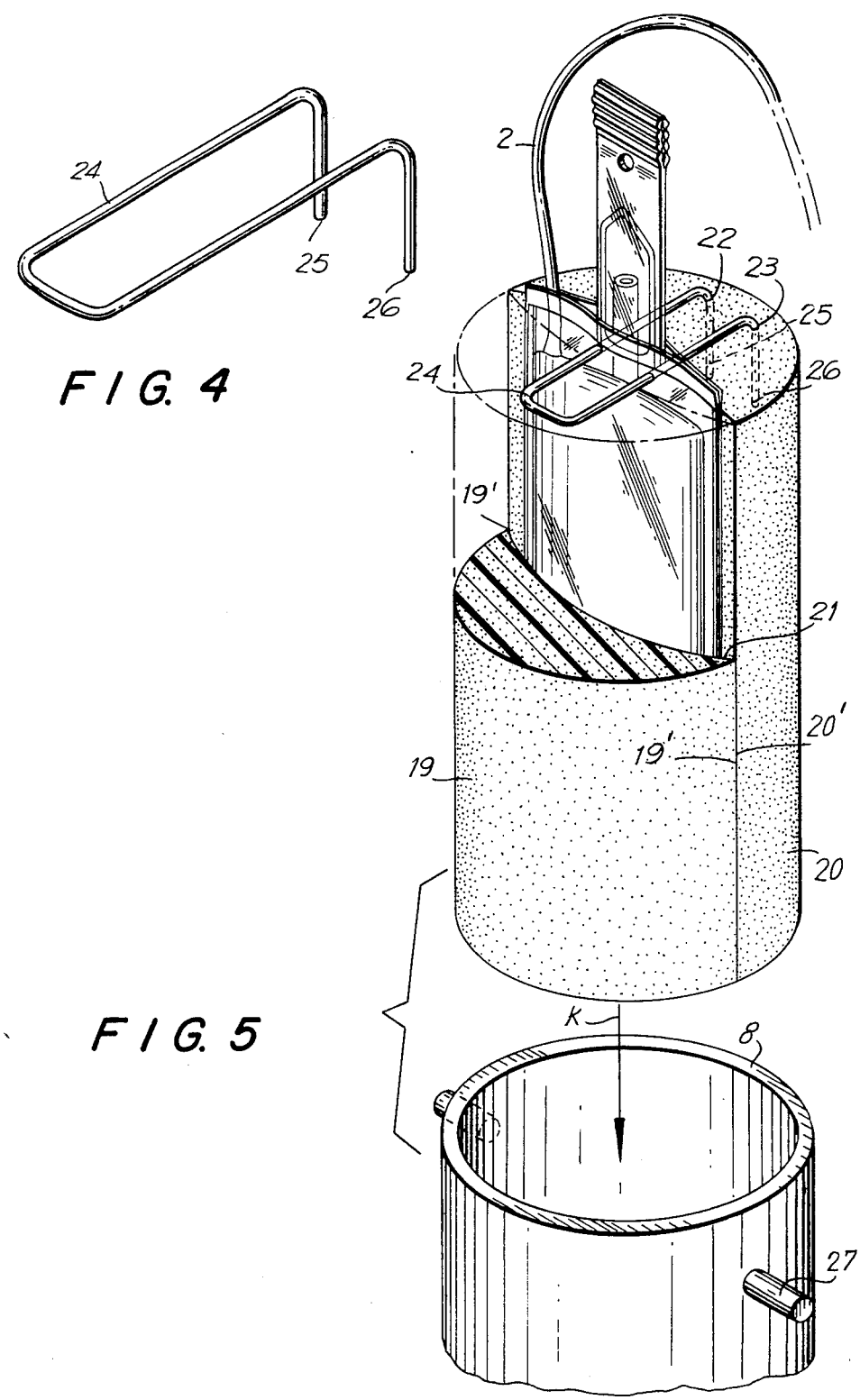
F I G. 4
F I G. 5

METHOD AND APPARATUS FOR USE IN PREPARATION OF FIBRINOGEN FROM A PATIENT'S BLOOD

BACKGROUND OF THE INVENTION

The present invention relates generally to the preparation of concentrated fibrinogen from blood for making fibrin glue and, more particularly, to the autologous preparation of relatively small quantities of concentrated fibrinogen for making fibrin glue.

Fibrin glue has been found to have widespread applications in various medical and surgical procedures. For example, fibrin glue is used as an adhesive for sealing various internal wounds or incisions in body organs. The glue also serves as a good tissue adhesive. Concentrated fibrinogen, which is used in making the fibrin glue, is initially prepared from human blood and stored for use at a later time during surgery.

A description of a technique for preparing fibrin glue from blood may be found, e.g., in Vascular Surgery, Volume 17, No. 5, September/October 1983, pp. 294–304. Generally, the amount of blood is collected and, after addition of sodium citrate as an anti-coagulant, centrifuged to form supernatant plasma. The plasma is collected and then frozen, e.g., at −80° C. for at least 6 hours. The frozen plasma can be stored for periods of over one year. Just prior to surgery, the frozen plasma is thawed at 4° C. for six hours. The thawed plasma is cold centrifuged to obtain a sediment of concentrated fibrinogen. Thrombin is added to the fibrinogen during the surgical procedure to produce fibrin glue for administration to the patient.

While this technique for preparing concentrated fibrinogen from the blood of one individual and administering fibrin glue produced from the fibrinogen to another individual has been widely adopted in Europe, its use is not presently permitted in the United States due to the possibility of transmission of infectious diseases, such as hepatitis or AIDS, from one individual to another. Accordingly, in the United States, only autologous synthesis and use of fibrin glue, i.e., preparation of the fibrin glue from the patient's own blood for use during his own imminent surgery is permitted. However, such autologous synthesis of fibrin glue has suffered from several drawbacks.

For example, it has not been possible to prepare relatively small quantities of concentrated fibrinogen for immediate use in a practical manner. The equipment and instruments for extracting the fibrinogen are generally large and located at places remote from the operating room. Such equipment is not suited for extraction and production of small quantities of fibrinogen.

Furthermore, since the preparation of larger quantities of concentrated fibrinogen requires longer times, the patient may be required to be admitted to the hospital earlier than otherwise indicated in order to provide sufficient time for the preparation of fibrinogen.

For these reasons, autologous preparation and use of fibrin glue has not been actively pursued in medical and surgical treatment in the United States.

SUMMARY OF THE INVENTION

Accordingly, it is an object of the present invention to provide new and improved methods and apparatus for use in the preparation of concentrated fibrinogen and fibrin glue.

Another object of the present invention is to provide new and improved methods and apparatus for use in autologous preparation of concentrated fibrinogen and fibrin glue produced therefrom.

A further object of the present invention is to provide new and improved methods and apparatus for use in autologous preparation of concentrated fibrinogen by which such production is completed in a more rapid manner than has been possible heretofore.

A still further object of the present invention is to provide new and improved methods and apparatus for use in autologous preparation of concentrated fibrinogen in more appropriate smaller quantities than has been practical heretofore.

Yet another object of the present invention is to provide new and improved methods and apparatus for use in autologous preparation of concentrated fibrinogen by which fibrin glue produced therefrom has improved tensile strength.

Briefly, these and other objects are obtained by providing an arrangement by which the centrifuging steps used in the preparation of the concentrated fibrinogen from which the fibrin glue is prepared are rendered specifically applicable to autologous preparation from a patient's own blood for administration to the same patient during imminent surgery. The arrangement comprises a small flat bag or packet into which the blood or plasma to be centrifuged is transferred, and an insert fixture assembly for receiving the packet and reliably securing the same in the centrifuge cup in a suitable orientation.

In an illustrated embodiment, the insert fixture assembly includes a cylindrical fixture comprising a pair of substantially semi-cylindrical parts having concave mating surfaces which define a recess between them in which the blood or plasma-containing packet is held by means of interengaging side edges of the mating surfaces and a support member attached to one of the fixture parts. The outer cylindrical configuration of the fixture permits the fixture which holds the blood or plasma-containing bag to be snugly fit within the centrifuge cup with the packet oriented in a suitable direction.

The arrangement of the invention permits smaller quantities of concentrated fibrinogen to be extracted from the blood in a shorter time than has been possible heretofore. The flat bag or packet provides maximum surface area on which the sediment of concentrated fibrinogen can be deposited.

BRIEF DESCRIPTION OF THE DRAWINGS

A more complete appreciation of the present invention and many of the attendent advantages thereof will be readily understood by reference to the following detailed description when considered in connection with the accompanying drawings in which:

FIG. 2 is a perspective view, partially broken away, of a conventional centrifuge rotor for use in a method in accordance with the invention;

FIG. 3 is a side elevation view of the packet comprising one component of apparatus in accordance with the invention;

FIG. 4 is a perspective view of a support member comprising one component of an insert fixture assembly in accordance with the present invention; and FIG. 5 is an exploded perspective view, partially broken away, illustrating a packet held in an insert fixture assembly in accordance with the invention and further illustrating insertion of the assembly into a centrifuge cup.

DESCRIPTION OF THE PREFERRED EMBODIMENTS

Figure 1:
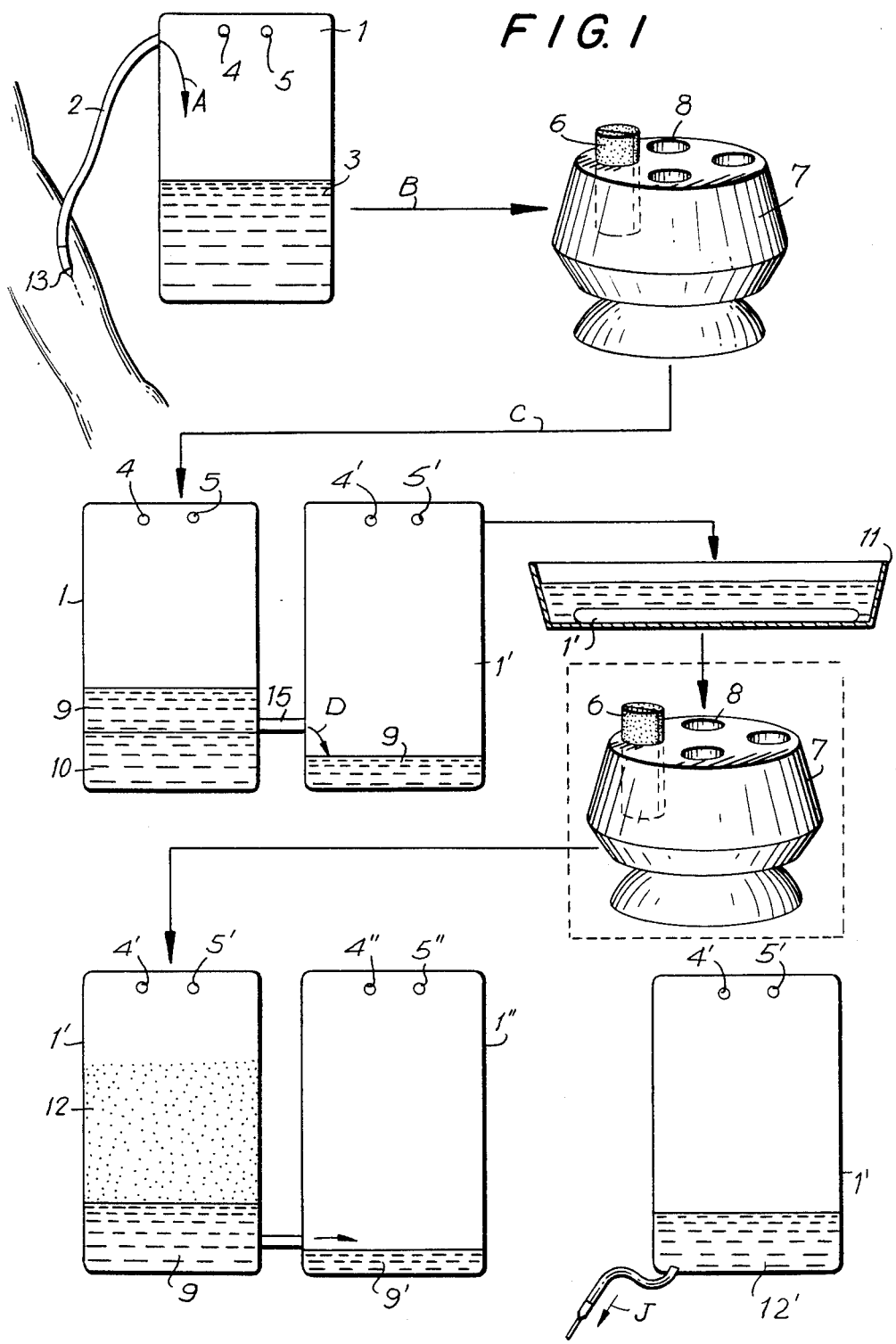
FIG. 1 is a schematic illustration showing the various steps in autologous preparation of concentrated fibrinogen utilizing a method and apparatus in accordance with the invention.

Referring now to the drawings wherein like reference characters designate identical or corresponding parts throughout the several views, and more particularly to FIG. 1, a method of autologous preparation of concentrated fibrinogen and fibrin glue in accordance with the invention will now be described. As illustrated in FIG. 1, blood 3 is extracted from the patient in a conventional manner by a syringe 13, and is transferred through a tube 2 into a flat bag or packet 1, preferably formed of plastic. The blood is mixed with an anticoagulant in packet 1. The packet 1 is of a relatively small size, e.g., 150 ml capacity. For example, a Transfer Pack available from Fenwal Laboratories, a division of Travenol Laboratories, Inc. of Deerfield, Illinois may be utilized. The packet 1 is substantially rectangular and has a pair of apertures 4 and 5 formed through its top.

The packet 1 is positioned in a substantially cylindrical insert fixture assembly 6 and the fixture assembly 6 holding packet 1 is placed in one of the cups 8 of a conventional centrifuge 7. For example, the centrifuge may be a Sorvall Model H-4000 provided with a model HG-4L swinging bucket rotor.

The blood 3 is centrifuged, for example, at 2000 rpm for about 5 minutes to separate the same into plasma supernatant 9 and sediment 10 of red blood cells. The plasma supernatant 9 is transferred through a plasma extractor 15 into a second packet 1', similar to the first packet 1, provided with apertures 4' and 5'. At this point, the plasma 9 in the second packet 1' is frozen, e.g., for about one hour at $-80°$ C. The frozen plasma 9 is then thawed by placing the packet 1' into a circulating water bath 11. Thawing takes place after 15 to 30 minutes at a bath temperature of $-4°$ C. to $-2°$ C., and can be accelerated by manually breaking-up the frozen contents of the packet 1' to increase the surface area thereof.

The second packet 1' is then removed from the waterbath 11 and quickly placed within the fixture assembly 6 whereupon the fixture assembly holding packet 1' is inserted into a cup 8 of centrifuge 7. Centrifuging of the plasma is then carried out in a controlled temperature environment, e.g., at a temperature of about 0° C. to +4° C., at about 4000 rpm for about 10 minutes.

The second centrifuging step results in the separation of the plasma into supernatant plasma 9' and cryoprecipitate 12 of concentrated fibrinogen, the latter being deposited on the interior surfaces of packet 1'. The supernatant plasma 9' is transferred into a third packet 1" similar to packets 1 and 1'. The cryoprecipitate 12 adhering to the interior surfaces of the second packet 1' remains.

The frozen cryoprecipitate 12 of concentrated fibrinogen is allowed to melt into a liquid 12' by allowing the packet 1' to reach room temperature. Thus, the cryoprecipitate turns to liquid within a few minutes and can be extracted with a tuberculin syringe 28. Extraction of the liquid cryoprecipitate is facilitated by injecting about 10 cc of air into the second packet 1'.

The concentrated fibrinogen 12' in liquid form is administered to the situs of application, e.g., a wound or incision in the patient, with a substantially equal amount of thrombin then also being applied to form the fibrin glue. After about one minute, the fibrinogen is converted in situ to fibrin glue.

The blood in the first packet 1 may be centrifuged for about 3 to 10 minutes at a temperature of about 0° C. to +5° C. with the supernatant plasma then being frozen at a temperature of about $-40°$ C. to $-100°$ C. for about $\frac{1}{2}-1\frac{1}{2}$ hours, the frozen plasma then being thawed at a temperature of about 0° C. to +5° C. for about 15 to 30 minutes. The thawed plasma is then centrifuged in the second packet 1' at about 0° C. for about 5 to 20 minutes. Thus, only about 40 to 50 ml of blood need be extracted from a patient to produce about 1 to 1.5 ml of the fibrinogen cyroprecipitate that is required to form the glue.

Referring to FIG. 2, the centrifuge 7 comprises a rotor 14 to which four cylindrical cups 8 are pivotally connected. Such a centrifuge 7 is usually found in most hospitals and medical centers. Each of the cups 8 is designed to hold a large quantity of liquid, e.g., about 1000 to 1500 ml, to be centrifuged. This is a considerable amount and much greater than any amount of blood or plasma that is to be centrifuged for synthesizing fibrinogen for the fibrin glue. In particular, only about 45 millileters of blood is required to be centrifuged in the autologous preparation of fibrin concentrate. It is therefore seen that the conventional centrifuge is generally not suitable for centrifuging the small amount of blood and plasma required in the autologous preparation of fibrin glue.

Referring to FIG. 3, packet 1 is generally flat and comprises apertures 4 and 5 at its upper end as described above. A feed tube 2 communicates with the interior of the packet 1 and a second conduit 16 which is normally sealed at 17 between two lips or extensions 18 (only one shown) also communicates with the interior of packet 1. The important characteristic of the packet is that it be generally flat and have a relatively small capacity, e.g. about 150 ml.

Referring to FIGS. 4 AND 5, the insert fixture assembly 6 which is inserted into one of the centrifuge cups 8 in the direction of arrow K (FIG. 5) comprises a pair of substantially semi-cylindrical parts 19 and 20 and a support member 24. The parts 19 and 20 have concave mating surfaces which abut along their axial side edges 19' and 20' to define a recess 21 between the mating surfaces. It will be understood that the particular shape of the recess 21 formed between the mating surfaces of parts 19 and 20 is not limited to this particular shape although it is desirable that the packets 1 and 1' seat against the surfaces of the recess 21 to the maximum extent possible. Therefore, as seen in FIG. 2, the long edges of packets 1 and 1' will be sandwiched between the side edges 19' and 20' of parts 19 and 20 so that the packets 1 and 1' are securely held in the cylindrical fixture within recess 21.

Referring to FIG. 4, the support member 24 is substantially U-shaped and comprises bent edges 25, 26 which are adapted to fit into respective holes 22 and 23, formed in one of the parts 19 or 20 as seen in FIG. 5. The legs of the support member 24 are adapted to pass through respective apertures 4, 5; 4', 5' of packet 1; 1' so that the packet 1; 1' is preferably seated against the internal mating surfaces of parts 19 and 20 as seen in FIG. 5 when the respective ends 25 and 26 of the support member 24 are inserted into the holes 22 and 23 of the insert fixture assembly 6. In this manner, the packet 1; 1' will be retained within the recess 21 formed between he internal mating surfaces of parts 19 and 20 and will be seated against at least one of the internal surfaces of these parts.

The use of the support member in fixing the packet within the recess of the cylindrical fixture prevents any torsion from being applied to the packet. The recess 21 between parts 19 and 20 is formed so that a packet 1 or 1' containing the blood or plasma contacts as much of the internal concave surfaces of the parts 19 and 20 as possible. This provides a secure seating of the packet 1 or 1' within the cylindrical fixture 6 allowing for effective separation of the blood or plasma component as noted above.

As illustrated in FIGS. 2 and 5, the centrifuge cups 8 are pivotally mounted to the rotor to swing outwardly about an axle 27 which defines the pivot axis of each cup. As seen in FIG. 5, the cylindrical insert fixture assembly 6 is inserted into the cup 8 so that a plane passing through the flat bag or packet substantially contains the pivot axis of the cup. This orientation promotes uniformity and efficiency of the centrifuging operation despite the relatively small quantities of blood and plasma being centrifuged.

The cylindrical insert fixture assembly 6 is shaped so as to fit snugly within the centrifuge cup 8, as illustrated in FIG. 5. In particular, the insert fixture assembly 6 formed by parts 19 and 20 is shaped to have dimensions complementary with the interior dimensions of the cup 8. When the parts 19 and 20 are thus inserted within a cup 8, the parts are held fast against each other to clamp or sandwich the edges of the packet between the side edges 19' and 20' of parts 19 and 20. In the illustrated embodiment, the insert fixture assembly preferably has a length of about 5 to 8 inches, a diameter of about 3 to 5 inches and recess 21 has a volume of about 5 to 15 cubic inches to accommodate the packet 1 or 1'. The insert fixture assembly 6 has a length of about 6 inches and a diameter of about 3⅝ inches with the recess 21 having concavely curved surfaces. The support member 24 is about 2½ inches long and the bent ends 25 and 26 each have a length of about 1 inch. The parts 19 and 20 are preferably constructed of styrofoam material.

As noted above, the invention enables smaller quantities of fibrinogen to be prepared more quickly than has been possible heretofore, thereby making autologous preparation of fibrin glue practical. The invention will be explained further by way of the following example:

EXAMPLE

A portable kit for preparation of fibrin glue from fibrinogen in accordance with the present invention, is prepared to contain 3.8% sodium citrate, bacteriostatic water, a 60-ml sterile syringe 13, three Fenwal Transfer Pack Units 1, 1', 1", one Sample Site (plasma) Extractor 15 (Fenwal), an 8- by 8- by 2- inch polyethylene tray 11, two styrofoam parts 19 and 20, one wire clamp support member 24, a submersible battery-operated pump conventionally available from Edmund Scientific, two alligator clip leads and a battery holder containing two D-cell batteries conventionally available from Radio Shack, unreconstituted bovine thrombin, and two sterile tuberculin syringes 28 with plastic cannulas.

Preparation of the fibrinogen and fibrin glue is done directly at the blood bank, i.e. in the hospital or medical center during or just before surgery. The temperature of centrifuge 7 was set at 4° C., with the polyethylene tray 11 being partially filled with 0.9% saline solution and placed inside the centrifuge 7 to prepare the 4° C. waterbath. The 46.7% sodium citrate was diluted to 3.8% by addition of the bacteriostatic water, at one part of citrate to 11 parts water. 5 ml of the dilute citrate was drawn into the 60 ml syringe 13, 45 ml of blood was collected into the citrate containing syringe 13 (FIG. 1). Gentle motion of the blood-containing syringe 13 ensures proper anticoagulation.

The blood was then transferred into a Transfer Pack unit or packet 1 through the side port tubing 2. About 10 cc of air was retained in the packet 1 to provide necessary volume during the subsequent centrifuging. The side tubing 2 was then sealed, and cut at a distance of one inch from the packet 1.

The substantially U-shaped support member 24 was then inserted through the holes 4 and 5 located at the upper edge of the packet 1. The packet 1 was then disposed between parts 19 and 20 as illustrated in FIG. 5, with the prongs 25 and 26 of the support member 24 being inserted into respective holes 22 and 23 in the sleeve member 20. The insert fixture assembly was then introduced into one of the centrifuge cups or buckets 8 as seen in FIG, 5. A cup 8 opposite the cup into which the sleeve 6 was inserted, was then balanced, with centrifuging then proceeding at 2000 rpm for five minutes at 4° C. The resulting supernatant plasma 9 (FIG. 1) was transferred into a second packet or bag 1' using the plasma extractor 15. This supernatant plasma 9 was then frozen at −80° C. for one hour.

The circulating waterbath was prepared by placing the submersible pump into the saline tray 11 (FIG. 1) located inside the centrifuge, with proper connection of leads to the batteries. The frozen plasma was then placed in the circulating waterbath 11, and allowed to thaw for between 15 and 30 minutes. The thawing could be accelerated by manually breaking-up the frozen contents to increase surface area.

The second packet was then removed from the bath 11, quickly disposed into the insert fixture assembly 6 in the same manner as the first packet 1, and secured with the clamp 24. The assembly was again inserted into a cup 8 of the centrifuge, with the opposite cup being balanced, and centrifuging then proceeding at 4000 rpm for ten minutes. This second centrifuging step formed supernatant plasma 9' and cryoprecipitate deposit 12 along the internal walls of the packet 1'. All the supernatant plasma 9' was removed into a third packet 1" with the plasma extractor 15, leaving the cryoprecipitate 12 adhering to the internal wall of the second packet 1'.

Within a few minutes, e.g. about five to 10 minutes, the cryoprecipate deposit 12 turns into liquid, and is extracted with a tuberculin syringe 28 and is ready for use. Injection of about 10 cc of air into the second transfer packet 1' facilitates the extraction in the direction of arrow J. About 1-1.5 ml of cryoprecipitate is formed from the 45 ml of blood initially extracted.

Next, a few drops of the reconstituted thrombin was added to the fibrinogen concentrate that was removed, to convert the fibrinogen into fibrin glue. The resulting fibrin glue is easily applied to the situs of an injury, wound, or incision, of the patient with a tuberculin syringe 28 fitted with a Teflon cannula.

The entire preparation of the fibrin glue from the initial withdrawal of blood from the patient, is accomplished well within three hours. This is in contrast to the previously utilized procedures, which required at least twelve hours to prepare the required glue product. At the same time, much smaller quantities of the fibrin glue can be prepared.

Furthermore, repeated studies have confirmed that the fibrin glue prepared in accordance with this technique, exhibits a tensile strength of at least 3 g/mm$^2$.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. A method for use in the autologous preparation of fibrin glue wherein a patient's blood is separated in a centrifuge having cylindral cups pivotally mounted to a rotor to obtain plasma and wherein the plasma is separated in the centrifuge to produce concentrated fibrinogen, comprising the steps of:
   (A) transferring the blood or plasma into a substantially flat packet;
   (B) fixing the packet containing the blood or plasma in a recess of a substantially cylindrical insert fixture assembly;
   (C) inserting said cylindrical-shaped insert fixture assembly in a cup of the centrifuge having a complementary cylindrical shape so that the insert fixture assembly is held snugly within said centrifuge cup;
   (D) centrifuging the blood or plasma contained within said packet fixed in said insert fixture assembly held in said centrifuge cup to separate the blood or plasma into components; and
   (E) forming fibrin glue from one of said separated components.

2. Method of claim 1 comprising the additional steps of:
   extracting blood from the patient;
   mixing the blood with anti-coagulant;
   carrying out steps (A)-(D) to form supernatant plasma;
   transferring the supernatant plasma to a second substantially flat packet;
   freezing said plasma in said second packet;
   thawing said plasma in said second packet;
   repeating steps (A)-(D) with said second packet containing the plasma to form liquid plasma and fibrinogen cryoprecipitate which adheres to the interior walls of the second packet;
   withdrawing the liquid plasma from the second packet;
   allowing said fibrinogen cryoprecipitate to melt into a liquid;
   withdrawing said liquid fibrinogen from the second packet; and
   mixing said fibrinogen with thrombin to form fibrin glue 3. The method of claim 2 wherein:
   the blood is centrifuged for a time in the range of about 3 to 10 minutes;
   the supernatant plasma is frozen for a time in the range of about $\frac{1}{2}$ to $1\frac{1}{2}$ hours;
   the frozen plasma is stored for a time in the range of between of about 15 to 20 minutes; and
   the thawed plasma is centrifuged for a time in the range of between about 5 to 20 minutes.

4. The method of claim 3, wherein:
   the blood is centrifuged at a temperature in the range of between about 0° C. to 5° C.;
   the plasma is frozen at a temperature in the range of between about $-40°$ C. to $-100°$ C.;
   the frozen plasma is thawed at a temperature in the range of beteen about 0° C. to 5° C.; and
   the thawed plasma is centrifuged at a temperature in the range of between about 0° C. to 5° C.

5. The method of claim 1, wherein:
   about 40 to 50 ml of blood is extracted from the patient; and
   about 1 to 1.5 ml of the fibrinogen cryoprecipitate is produced.

6. The method of claim 1, wherein the step of inserting the cylindrical shaped insert fixture assembly into the cup of the centrifuge is carried out so that a plane containing the flat packet also contains the pivot axis of the centrifuge cup.

7. The method of claim 1 wherein said substantially flat packet has relatively small capacity.

8. The method of claim 7 wherein said substantially flat packet has a capacity of about 150 ml.

* * * * *